United States Patent
Yabuki et al.

(10) Patent No.: US 7,608,459 B2
(45) Date of Patent: Oct. 27, 2009

(54) METHOD FOR THE DETERMINATION OF BODY ODOR

(75) Inventors: Masayuki Yabuki, Sumida-ku (JP);
Yoshihiro Hasegawa, Sumida-ku (JP);
Shun Nakamura, Haga-gun (JP)

(73) Assignee: Kao Corporation, Tokyo (JP)

( * ) Notice: Subject to any disclaimer, the term of this patent is extended or adjusted under 35 U.S.C. 154(b) by 298 days.

(21) Appl. No.: 11/568,778

(22) PCT Filed: Apr. 25, 2005

(86) PCT No.: PCT/JP2005/007835

§ 371 (c)(1),
(2), (4) Date: Nov. 7, 2006

(87) PCT Pub. No.: WO2005/108980

PCT Pub. Date: Nov. 17, 2005

(65) Prior Publication Data

US 2008/0014649 A1    Jan. 17, 2008

(30) Foreign Application Priority Data

May 11, 2004    (JP) .............................. 2004-141244

(51) Int. Cl.
*G01N 33/50* (2006.01)
*C07C 229/02* (2006.01)
(52) U.S. Cl. ...................... 436/111; 562/556
(58) Field of Classification Search ................. 436/111; 562/556
See application file for complete search history.

(56) References Cited

FOREIGN PATENT DOCUMENTS

JP    2001 220593    8/2001
JP    2001 271088    10/2001

OTHER PUBLICATIONS

Starkenmann, Christian et al., Identification of the Precursor of (S)-3-Methyl-3-sulfanylhexan-1-ol, the Sulfury Malodor of Human Axilla Sweat, Chemistry & Biodiversity, 2005, vol. 2, pp. 705-716.*
Natsch, Andreas et al., Identification of Odoriferous Sulfanylalkanols in Human Azilla Secretions and Their Formation through Cleavage of Cysteine Precursors by a C-S Lyase Isolated from Axilla bacteria, Chemistry & Biodiversity, 2004, vol. 1, pp. 1058-1067.*
Wouter H. Hendriks et al., "Felinine: A Urinary Amino Acid of Felidae", Comp. Biochem. Physiol., vol. 1128, pp. 581-588, 1995.

* cited by examiner

*Primary Examiner*—Walter D Griffin
*Assistant Examiner*—Christine T Mui
(74) *Attorney, Agent, or Firm*—Oblon, Spivak, McClelland, Maier & Neustadt, L.L.P.

(57) ABSTRACT

A method for determining potential for body odor and a method for determining the effectiveness of a deodorant carried out by detecting a substance represented by the following formula (1) or a derivative thereof:

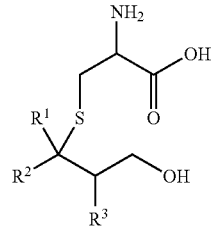

Formula 1 wherein $R^1$ is a hydrogen atom or a methyl group, $R^2$ is an alkyl group containing 1 to 5 carbon atoms, and $R^3$ is a hydrogen atom or a methyl group.

15 Claims, 3 Drawing Sheets

METHOD FOR THE DETERMINATION OF BODY ODOR

FIELD OF THE INVENTION

This invention relates to a method for determination of the possibility of body odor generation, and in particular, apocrine odor generation. This invention also relates to a method for determination of the effectiveness of a deodorant.

BACKGROUND OF THE INVENTION

With the recent increase in hygiene consciousness, an increasing number of people are concerned about their body odor. The term "body odor" is a generic term for the odor or smell generated in various parts of the body, and main sources of the odor or smell include the head, mouth, armpit, groin, and foot sole. Among such sources of the odor or smell, the armpit smell is easily detected by the person himself/herself or by the people in the immediate area of the person, and the factors such as presence/absence, strength, and qualitative difference of the armpit smell greatly affect the systemic body odor. Therefore, it is often the armpit smell and not the body odor in general that is annoying for the person himself/herself or for the people in the immediate area of the person.

The armpit smell comprises a sour and stuffy smell and a smell specifically found in the armpit. The sour and stuffy smell is generated by decomposition of the eccrine sweat and grime secreted by the eccrine gland by the action of the indigenous bacteria of the skin. The main cause of this smell is lower carboxylic acids containing 2 to 5 carbon atoms, and this smell is called a "lower fatty acid smell", or more simply, an "acid smell". In contrast, the smell specific to the armpit is generated by decomposition of apocrine sweat secreted from the apocrine gland containing proteins and cholesterol at a high concentration by the action of the indigenous bacteria of the skin, and this smell is called the "apocrine odor" or "armpit smell" (hereinafter referred to as the "apocrine odor").

Accordingly, for those people who are conscious about their body odor, and in particular, the armpit smell, it would be quite important to know the degree of their apocrine odor that they originally have in their armpit, and whether their own effort of reducing the body odor, for example, by the use of deodorant products or surgical removal of the apocrine gland, actually had some effects.

Conventional methods that have been used in finding the degree presence or strength) of one's own apocrine odor in the armpit include (1) a sensory test in which the armpit smell is evaluated by a third person, (2) an estimation based on information such as the presence of a person with the armpit smell in his or her family and moist cerumen, and the like which are said to be related to the apocrine odor.

However, the method (1) is associated with the difficulty of a quantitative assessment due to the large margin of the subjective decision of the panelist and assessment error due to olfactory fatigue. In the meanwhile, the method (2) does not directly assess the apocrine odor in the armpit, and this method cannot be used in an objective and quantitative determination of the effectiveness of the improvement of the armpit smell by the use of deodorant products or the effect of the surgical removal of the apocrine gland.

Conventional methods that have been used to determine the effectiveness of the deodorant which is expected to suppress the apocrine odor generation include (1) a method in which the candidate deodorant is applied to the armpit of the test subjects, and the smell of the armpit is evaluated after the application, and (2) a method in which the candidate deodorant is mixed with the sweat collected from the armpit of the test subject, and the smell of the mixture is evaluated after an adequate incubation of the mixture.

Both of these methods, however, are associated with the considerable burden of the test subjects and this leads to the difficulty of evaluating a large number of candidate deodorants under the same conditions. In addition, quantitative assessment is difficult due to the large margin of the subjective decision of the panelist and assessment error due to olfactory fatigue. Furthermore, such method is associated with the difficulty in differentiating whether it was the generation of the apocrine odor that was suppressed by the candidate deodorant; whether the apocrine odor that had been generated was deodorized; or whether the apocrine odor was sensed to a lower degree by the presence of another odor. Accordingly, an accurate, efficient, objective, and quantitative determination of the "effectiveness in suppressing the apocrine odor generation" has been difficult.

The inventors of the present invention investigated odor components in the human armpit, and found that the main components responsible for the apocrine odor are alcohol compounds having a thiol group at position 3 (hereinafter sometimes referred to as 3-mercapto alcohol compound) as typically represented by 3-mercapto-3-methylhexane-1-ol, 3-mercaptohexane-1-ol, 3-mercaptopentane-1-ol, 3-mercapto-2-methylbutane-1-ol, and 3-mercapto-2-methylpentane-1-ol (Non-patent document 1).

The inventors of the present invention also found that 3-mercapto-3-methylhexane-1-ol is present at a mass ratio of 10 or more times higher than that of other 3-mercapto alcohol compounds, and that this 3-mercapto-3-methyl-hexane-1-ol is the most common 3-mercapto alcohol compound in the armpit of people having apocrine odor (Non-patent document 1).

The inventors of the present invention also found that the 3-mercapto-3-methylhexane-1-ol is an optically active substance comprising 72% by mass of (S)-3-mercapto-3-methylhexane-1-ol and 28% by mass of (R)-3-mercapto-3-methylhexane-1-ol (Non-patent document 1).

Patent Document 1 discloses that, as flavoring components, 3-mercapto-2-methylbutane-1-ol has the characteristic odor like grass, leek, or gas, (S)-3-mercaptohexane-1-ol has a grass or rustic odor, and (R)-3-mercaptohexane-1-ol has odor like a grapefruit/passion fruit, gooseberry, or onion.

[Non-patent document 1] Japanese Journal of Taste and Smell Research vol. 10, No. 3, pages 807-810 (December 2003).

[Patent Document 1] JP-A-2001-2634.

DISCLOSURE OF THE INVENTION

The present invention has enabled an objective and quantitative determination of the body odor, and in particular, latent apocrine odor, namely, the possibility (potential) of apocrine odor generation in the armpit by detecting the substance represented by formula (1) as described below. The present invention has enabled an objective and quantitative determination of the degree (presence/absence or strength) of apocrine odor by using the 3-mercapto alcohol compound as described above for the index.

The present invention has also enabled an accurate, efficient, objective, and quantitative determination of the effectiveness of a deodorant which suppresses generation of body odor, in particular, the apocrine odor in the armpit by quantitatively measuring the substance represented by formula (1) as described below.

Accordingly, this invention provides a method for determining potential for body odor carried out by detecting a substance represented by the following formula (1):

Formula (1)

or its derivative wherein $R^1$ is a hydrogen atom or methyl group and $R^2$ is an alkyl group containing 1 to 5 carbon atoms, and $R^3$ is a hydrogen atom or methyl group.

This invention also provides a method for determining effectiveness of a deodorant carried out by quantitatively measuring a substance represented by formula (1).

The substance represented by formula (1) has an amino group and a carboxy group. The substance represented by formula (1) is believed to be present in the interior or the exterior of the body in the state in which the amino group and/or the carboxy group has formed a salt, or in the state with a higher molecular weight in which the amino group and/or the carboxy group has formed a peptide bond with various amino acids a peptide made of various amino acids, or a protein made of various amino acids.

The present invention also provides a method for determining potential of body odor by detecting a derivative of the substance represented by formula (1), namely, a derivative in which the amino group and/or the carboxy group of such substance has formed a salt (for example, a hydrochloride or a metal salt), a derivative in which the amino group and/or the carboxy group has formed a peptide bond with various amino acids (for example, a dipeptide), or a derivative in which the amino group and/or the carboxy group has formed a peptide bond with an atomic group formed by condensation with dehydration of at least 2 molecules of at least one member selected from various amino acids (for example, a tripeptide, an oligopeptide, a polypeptide, or a protein). The present invention also provides a method for determining the effectiveness of a deodorant by quantitatively measuring such a derivative.

In the present invention, detection of the substance represented by formula (1) or its derivative at a high sensitivity have been enabled by chemically modifying the substance represented by formula (1) and/or its derivative, in particular, by chemically modifying a functional group of such substance and/or its derivative, and detecting the substance represented by formula (1) and/or its derivative which has been chemically modified, and as a consequence, the present invention has enabled to carry out the determination of the possibility (potential) of generation of the apocrine odor and the determination of the effectiveness of the deodorant at higher objectivity and quantitative accuracy.

The present invention also provides a method for determining potential of the body odor or a method for determining effectiveness of a deodorant in which the determination carried out by detecting the substance represented by formula (1) having a chromophore which absorbs visible or UV light or a chromophore which emits fluorescence incorporated in at least one member selected from an amino group, carboxy group, and hydroxy group thereof. The present invention also provides a method for determining potential of the body odor or a method for determining effectiveness of a deodorant in which the determination carried out by detecting the substance represented by formula (1) or its derivative having a chromophore which absorbs visible or UV light or a chromophore which emits fluorescence incorporated in at least one functional group thereof.

This invention also provides a substance represented by the following formula (1a):

Formula (1a)

MODE FOR CARRYING OUT THE INVENTION

The inventors of the present invention made investigation on the method for objectively and quantitatively determining the possibility (potential) of apocrine odor generation in a state when the apocrine odor is not actually generated due to the effects of, for example, the surrounding environment (season, temperature, moisture etc), namely, in a latent state of the apocrine odor (namely, as a state not yet manifested).

The inventors of the present invention found, from the armpit of a person with apocrine odor, the substance represented by formula (1) as a previous stage substance (hereinafter also referred to as a "precursor") from which 3-mercapto alcohol compound which is the main substance responsible for the apocrine odor is formed. This precursor itself has no odor, and this is the significant difference of this precursor from the 3-mercapto alcohol compound which has a stinky beastly smell like that of sulfur.

The inventors of the present invention also confirmed that the substance represented by formula (1) changes into the 3-mercapto alcohol compound which is the main substance responsible for the apocrine odor by the action of, for example, the microorganisms on the skin. The inventors also found that such 3-mercapto alcohol compound is present in the armpit of a person having the apocrine smell, and that the amount of the 3-mercapto alcohol compound is proportional to the strength of the apocrine odor.

The present invention relates to a method for objectively and quantitatively assessing the possibility (potential) of the armpit smell generation, and in particular, apocrine odor generation by detecting the substance represented by formula (1). The present invention also relates to a method for accurately effectively, objectively and quantitatively assessing the effectiveness of a deodorant which is expected to suppress the generation of the armpit smell, and in particular, apocrine odor. The present invention also relates to a novel substance represented by formula (1a).

The present invention has enabled an objective and quantitative assessment of the body odor, in particular, the latent apocrine odor of the armpit, namely, the possibility (potential) of the apocrine odor generation by detecting the substance represented by formula (1) which is the substance of a previous stage of the main substance responsible for the apocrine odor or a derivative of the substance represented by formula (1). The present invention has also enabled an accurate, efficient, objective, and quantitative assessment of the effectiveness of a deodorant which is expected to suppress the apocrine odor generation.

The substance represented by formula (1) and the apocrine odor in the human armpit has the relation as described below.

i) The substance represented by formula (1) is an odorless substance found in the armpit of a person with the possibility (potential) of generating apocrine odor.

ii) The substance represented by formula (1) changes into a 3-mercapto alcohol compound which has a stinky and beastly smell like the smell of sulfur and which is the main substance responsible for the apocrine odor by the action of, for example, microorganisms on the skin.

The 3-mercapto alcohol compound as mentioned above is an alcohol compound which has a thiol group at position 3. Typical examples are 3-mercapto-3-methylhexane-1-ol, 3-mercaptohexane-1-ol, 3-mercaptopentane-1-ol, 3-mercapto-2-methylbutane-1-ol, and 3-mercapto-2-methylpentane-1-ol, which are represented by the following formula (2a) to (2e). These substances have the odor resembling apocrine odor.

Formula (2a):

3-mercapto-3-methylhexane-1-ol

Formula (2b):

3-mercaptohexane-1-ol

Formula (2c):

3-mercaptopentane-1-ol

Formula (2d):

3-mercapto-2-methylbutane-1-ol

Formula (2e):

3-mercapto-2-methylpentane-1-ol

The 3-mercapto alcohol compound detected from the armpit of a person with apocrine odor is a substance formed by the decomposition of the substance represented by formula (1) by the action of, for example, microorganism on the skin.

It is estimated that the substances represented by formulae (2a) to (2e) are not the only substances present in the armpit of a person with apocrine odor, and substances having a similar chemical structure should also be present in the armpit.

In addition, the amount of the 3-mercapto alcohol compound found in the armpit of a person with apocrine odor is proportional to the strength of the apocrine odor, and this means that the 3-mercapto alcohol compound is the main substance responsible for the apocrine odor of the human armpit.

Furthermore, in the armpit of a person with apocrine odor, the 3-mercapto-3-methylhexane-1-ol represented by formula (2a) is found at an amount in terms of the mass ratio 10 times or higher than the substances represented by formula (2b) to (2e), and at a highest frequency among such compounds in the armpit of a person with apocrine odor. In other words, the 3-mercapto-3-methyl-hexane-1-ol is the most important substance responsible for the apocrine odor of the human armpit.

2-amino-7-hydroxy-5-methyl-5-propyl-4-thiaheptanoic acid represented by the following formula (1a) is a novel substance which the inventors of the present invention found from the armpit of a person who may generate apocrine odor, and this substance is the substance of a previous stage (also referred to as the precursor) of the 3-mercapto-3-methylhexane-1-ol which is the most important substance responsible for the apocrine odor.

Formula (1a)

The precursor represented by formula (1a) is itself an odorless compound, and in this point, this compound is greatly different from the 3-mercapto-3-methylhexane-1-ol which has a stinky and beastly smell like sulfur. This precursor has the skeleton of 3-mercapto-3-methylhexane-1-ol (2a) which is the most abundant 3-mercapto alcohol compound in the armpit of a person with apocrine odor simultaneously with the skeleton of an α-amino acid.

This precursor has been estimated to be a condensate of an odorant substance and an α-amino acid formed by removal of water (or H₂S) from the thiol group of the 3-mercapto-3-methylhexane-1-ol and hydroxy group (or thiol group) of serine (or cysteine).

This substance represented by formula (1a) changes to 3-mercapto-3-methylhexane-1-ol (2a) which is the main substance responsible for the apocrine odor in the armpit of a person with apocrine odor by the action of, for example, the microorganisms on the skin.

Accordingly, among the substances represented by formula (1), the 2-amino-7-hydroxy-5-methyl-5-propyl-4-thiaheptanoic acid represented by formula (1a) is particularly suitable as a substance for use in determining the possibility (potential) of the apocrine odor generation in view of the relative abundance of this substance in the armpit of a person having apocrine odor and the resulting ease of detection, and the fact that it changes to the 3-mercapto-3-methylhexane-1-ol which is the substance most responsible for the apocrine odor by the action of, for example, microorganism on the skin. This substance has never been reported not to mention the report of the isolation, and nevertheless, this substance is particularly suitable as a substance for use as an index in the determination of the potential body odor. For the same reason, this substance is also particularly useful as a substance for use as an index in the determination of the effectiveness of the substance which is expected for the deodorant effects of the armpit smell, and in particular, apocrine odor.

The substances represented by formulae (2b) to (2e) which the inventors of the present invention found from the armpit of the person having apocrine odor are also estimated to be present as the substances represented by the following formulae (1b) to (1e) in the stage before turning into the respective odorant substances. These precursors are estimated to change to the substances represented by formulae (2b) to (2e) by the action of, for example, microorganism on the skin

(1b)

2-amino-7-hydroxy-5-propyl-4-thiaheptanoic acid

(1c)

2-amino-7-hydroxy-5-ethyl-4-thiaheptanoic acid (1d)

2-amino-7-hydroxy-5-methyl-6-methyl-4-thiaheptanoic acid (1e)

2-amino-7-hydroxy-5-ethyl-6-methyl-4-thiaheptanoic acid

It is estimated that the substances represented by formulae (1a) to (1e) are not the only substances present in the armpit of a person with apocrine odor, and substances having similar chemical structures may also be present in the armpit.

In the state when the substance represented by formula (1) is present in the armpit but has not turned into the substance represented by formula (2) which is the main substance responsible for the apocrine odor, the apocrine odor can be regarded as latent (namely, not yet manifested). Accordingly, the detection of the substance represented by formula (1) carried out in the present invention enables objective and quantitative determination of the possibility (potential) of the apocrine odor generation. The measurement of the substance represented by formula (1) also enables objective and quantitative determination of the effectiveness of the deodorant.

The 2-amino-7-hydroxy-5-methyl-5-propyl-4-thiaheptanoic acid represented by formula (1a) which is the substance which the inventors of the present invention found from the armpit of a person with apocrine odor has an amino group and carboxy group.

Since the substance represented by formula (1) is an amino acid derivative, the amino group may be present in the form of —NH₂ or —NH₃⁺, and carboxy group may be present in the form of —COOH or —COO⁻ depending on the pH conditions.

The amino group in formula (1) is estimated to be present in the interior and exterior of the body in the state of a salt (for example, hydrochloride); in the state bonded by a peptide bond to an α-amino acid selected from glycine, alanine, valine, leucine, isoleucine, proline methionine, phenylalanine, tryptophan, serine, threonine, cysteine, tyrosine, asparagine, glutamine, aspartic acid, glutamic acid, histidine, lysine, and arginine; or in the state bonded by a peptide bond to an atomic group formed by condensation with dehydration of at least 2 molecules of at least 1 member selected from the amino acid as described above.

The carboxy group in formula (1) is estimated to be present in the interior and exterior of the body in the state of a salt (for example, a metal salt); in the state bonded by a peptide bond to the amino acid as described above; or in the state bonded by a peptide bond to an atomic group formed by condensation with dehydration of at least 2 molecules of at least 1 member selected from the amino acid as described above.

In other words, the substance represented by formula (1) is estimated to be present with its amino group and carboxy group moieties forming a salt or bound to another peptide or protein.

Accordingly, in the present invention, the determination of the possibility (potential) of the apocrine odor generation can also be realized by detecting a derivative of the substance represented by formula (1) at the amino group, for example, a salt (for example, hydrochloride); a substance bonded by a peptide bond to an α-amino acid (for example, a dipeptide) selected from glycine, alanine, valine, leucine, isoleucine, proline, methionine, phenylalanine, tryptophan, serine, threonine, cysteine, tyrosine, asparagine, glutamine, aspartic acid, glutamic acid, histidine, lysine, and arginine; or a substance bonded by a peptide bond to an atomic group formed by condensation with dehydration of at least 2 molecules of at least 1 member selected from the amino acid as described above (for example, tripeptide, oligopeptide, polypeptide, and protein). The objective and quantitative determination of the effectiveness of the deodorant can also be realized by quantitatively determining a derivative of the substance represented by formula (1) at the amino group.

In the present invention, the determination of the possibility (potential) of the apocrine odor generation can also be realized by detecting a derivative of the substance represented by formula (1) at the carboxy group, for example, a salt (for example, a metal salt); a substance bonded by a peptide bond to the amino acid as described above (for example, a dipeptide); or a substance bonded by a peptide bond to an atomic group formed by condensation with dehydration of at least 2 molecules of at least 1 member selected from the amino acid as described above (for example, tripeptide, oligopeptide polypeptide, and protein). The objective and quantitative determination of the effectiveness of the deodorant can also be realized by quantitatively determining a derivative of the substance represented by formula (1) at the carboxy group.

Accordingly the derivative of the substance represented by formula (1) which is detected or quantitated in the present invention may include the derivatives as described above.

In the present invention, the body odor may be determined by further detecting the substance represented by formula (2) in addition to the substance represented by formula (1) or its derivative.

Formula 2 wherein $R^1$, $R^2$, and $R^3$ are as defined above.

Typical examples of the substance represented by formula (2) include the substances represented by formulae (2a) to (2e). These substances are generated by the action of, for example, microorganisms on the skin, and these are the main substances that cause apocrine odor.

Accordingly, a more comprehensive, objective and quantitative determination of the possibility (potential) of the armpit smell generation and the degree (presence/absence, strength, etc.) of the apocrine odor which has already been generated can be accomplished by detecting the substance represented by formula (2) which is the main substance responsible for the apocrine odor in addition to the substance represented by formula (1).

The present invention is also capable of determining the body odor by detecting a substance represented by the following formula (3), (4), (5), or (6).

Formula 3

Formula 4

Formula 5

Formula 6 wherein $R^1$, $R^2$ and $R^3$ are as defined above.

The substances represented by formulae (5) and (6) are the substances produced by decomposition of the substances represented by formulae (3) and (4), respectively, by the action of, for example, microorganisms on the skin, and these are the substances that cause apocrine odor.

Accordingly, latent apocrine odor, namely, the possibility (or potential) of the generation of apocrine odor can be objectively and quantitatively determined by further detecting the substance represented by formula (3) or (4), which is the substance before conversion into the substance represented by formula (5) or (6) that is responsible for the apocrine odor.

Furthermore, simultaneous detection of the substance represented by formula (5) or (6) that is responsible for the apocrine odor will enable an integral, objective, and quantitative determination of the possibility (or potential) of the generation of the apocrine odor together with the degree (presence/absence, strength, etc.) of the apocrine odor that has already been generated.

Next, the method of determining body odor by detecting a substance represented by any of formulae (1) to (6) and/or a derivative thereof is described in further detail by referring to typical embodiments.

The method for determination of the body odor according to the present invention is not particularly limited. The determination, however, may be accomplished by analyzing whether the substance of any one of formulae (1) to (6) and/or its derivative is present in the armpit by various chemical, physical, biological, or other analytical method, and determining the body odor based on the result of the analysis.

For example, determination of the body odor may be conducted by (1) collecting the substance present in the armpit, and (2) qualitatively analyzing whether there is a substance represented by any of formulae (1) to (6) and/or its derivative in the collected substance, and when the substance represented by any of formulae (1) to (6) and/or its derivative is present quantitatively analyzing the amount of such substance to thereby determine the body odor based on the comprehensive result of the analysis.

The substance in the armpit can be collected, for example, by rubbing the armpit with a fabric such as absorption wadding by spraying the armpit with physiological saline or the like and then wiping the armpit with a fabric such as absorption wadding, by sandwiching a cotton pad between the armpit for a predetermined period, or by wearing an underwear or a T shirt having a cotton pad fixed to the part that comes in contact with the armpit for a predetermined time, and such method may be used either alone or in combination of two or more methods.

Exemplary methods used for promoting the sweating in the armpit include application of exercise stress such as running and muscular training, application of temperature stress by entering a high temperature room such as a sauna, application of mental stress through mental arithmetic or viewing a horror movie, application or injection of a blood circulation accelerator such as pepper extract or sweat gland stimulant such as epinephrine on or in the skin of the armpit, and such method may be used either alone or in combination of two or more methods.

If desired, the method for collecting the substance in the armpit and the method for promoting sweating in the armpit can be used in combination.

In the present invention, the analyte collected from the armpit by the method as described above may be treated by various purification or concentration techniques using the difference in chemical and other properties of the substance represented by formula (1) from other substances to thereby facilitate detection of the substance represented by formula (1).

For example, the substance represented by formula (1) has a characteristic feature that it is readily soluble in water but not in oil, and therefore, oil soluble contents in the analyte may be separated by using the difference in solubility in water or oil to thereby increase the concentration of the substance represented by formula (1) in the analyte.

More specifically, oil soluble contents from sebum such as triglycerides and higher fatty esters can be removed from the analyte collected by the collection methods of the substances in the armpit as described above by adding an organic solvent such as hexane pentane, dichloromethane, or diethylether to the analyte and thoroughly stirring the mixture to thereby dissolve the oil-soluble content in the analyte in the organic solvent, separating the mixture into the aqueous layer and the organic layer by such means as centrifugation, and removing the oil-soluble content from the analyte together with the solvent to thereby facilitate detection of the substance represented by formula (1).

In the present invention, any of the substances represented by formulae (1) to (6) may be synthesized by chemical or other method, and the thus synthesized substance may be used for the standard.

As described in the following section, the substances represented by formulae (1) to (6) and/or their derivatives are substances that can be produced by chemical synthesis, and synthetic products with constant quality can be supplied in a stable manner.

For example, the substances represented by formulae (1) and (2) can be synthesized by the following reaction scheme (7). In this reaction scheme, a fatty ester derivative (a) having an unsaturated structure is used for the starting material, and benzyl mercaptan or the like is introduced to this fatty ester derivative (a) by addition to thereby produce a fatty ester derivative (b) having a thioether structure at position (3). This fatty ester derivative (b) is reduced by a reducing agent such as lithium aluminium hydride to produce an alcohol derivative (c) having a thioether structure at position 3.

The 3-mercapto alcohol compound represented by formula (2) is synthesized when a benzyl group is subsequently eliminated by Birch reduction. This 3-mercapto alcohol compound and 3-chloroalanine having its amino group protected with a tert-butoxycarbonyl group (BOC group) are condensed to produce an α-amino acid derivative (d) having a thioether structure, and the product is further treated with an acid (trifluoroacetic acid, etc) to eliminate the protective group. The substance represented by formula (1) is thus synthesized.

-continued (d) $\xrightarrow{H^+}$ (1)

wherein $R^1$, $R^2$, and $R^3$ are as defined above, $R^4$ is an alkyl group, and $R^5$ is benzyl group.

The substance represented by formula (1) has an α-amino acid skeleton. This substance is a component found from the human armpit, and configuration of the α carbon is an L-configuration. However, when the substance represented by formula (1) is used in the body odor determination by chemically synthesizing such substance, the substance is not particularly limited for its configuration, and an amino acid of D configuration and an amino acid mixture containing amino acids of both L and D configurations at any ratio can be used in addition to the amino acid of L configuration. For example, the 3-chloroalanine used in the synthesis as mentioned above may be any of L-3-chloroalanine, D-3-chloroalanine, DL-3-chloroalanine, or a 3-chloroalanine mixture containing any of these 3-chloroalanines at an arbitrary ratio.

The substance represented by formula (1) also has the skeleton of 3-mercapto-3-methylhexane-1-ol which is the main substance responsible for the apocrine odor.

The 3-mercapto-3-methylhexane-1-ol which is the main substance responsible for the apocrine odor is an optically active substance containing 72% by mass of (S)-3-mercapto-3-methylhexane-1-ol and 28% by mass of (R)-3-mercapto-3-methylhexane-1-ol. However, when the substance represented by formula (2) is chemically synthesized for body odor determination, the composition is not particularly limited, and it is possible to use the (S) or (R) form produced by selective synthesis by the asymmetric synthesis technique using an asymmetric catalyst such as transition metal or a mixture of such selectively synthesized forms at an arbitrary ratio.

Alternatively, a racemic body comprising 50% by mass of the (S) form and 50% by mass of the (R) may be synthesized and used with no further treatment, or after separating the (S) and (R) forms by any of the physical, chemical, biological or other technique such as crystallization or chromatography. When the (S) and (R) forms are separated, they may be used alone or after mixing at an arbitrary ratio.

Similarly, when the substance represented by formula (1) is produced by chemical synthesis, the substance represented by formula (2), namely, 3-mercapto-3-methylhexane-1-ol used for the starting material is not particularly limited for its configuration, and either one of (S) and (R) forms or a mixture of (S) and (R) forms at an arbitrary ratio can be used.

Since the substance represented by formula (1) has two asymmetric carbon atoms, as much as 4 isomers are present. The substance represented by formula (1) is not particularly limited for such configuration, and an as-synthesized product which is a mixture of such isomers at a certain ratio can be used either with no further processing or after separating into the isomers by various separation and purification techniques. The thus separated isomers may be used either alone or as a mixture of two or more at an arbitrary ratio.

In the determination of the body odor by detecting the substances represented by formulae (1) to (6), the determination can be carried out either by detecting such substance itself or by detecting a derivative of such substance. The determination may also be carried out by detecting both the substance itself and a derivative thereof.

The method used in the present invention in qualitatively and/or quantitatively assaying whether the substance collected from the armpit contains any of the substances represented by formulae (1) to (6) and/or its derivative is not particularly limited. Exemplary techniques include analysis by chromatographic separation and immunochemical assay (also referred to as "immunoassay") using, for example, a monoclonal antibody, and these techniques may be combined with various techniques such as chemiluminescence, chemical amplification, and electrochemical measurements, which are capable of realizing amplification or supersensitivity in the stage of the detection.

The chromatographic processes which may be used in the present invention are not particularly limited, and examples include liquid chromatography, gas chromatography, thin layer chromatography, and electrophoresis.

Liquid chromatography is a process wherein the solute is separated by the difference in the affinity for the stationary phase and the mobile phase, and the present invention can make use of various separation mechanisms (interaction between the elutes and the stationary phase). Examples include adsorption chromatography, partition chromatography, ion exchange chromatography, and size exclusion chromatography (gel filtration chromatography or gel permeation chromatography).

More specifically, in the adsorption column chromatography, for example, the separation is accomplished by the difference in the adsorption factor when the solute is adsorbed by the stationary phase through a physical or chemical process, and the components are separated from each other in the column and retained for the time inherent to each component (this time is called "retention time") and then eluted from the column to pass through the detector in the exterior of the column. In the case of the size exclusion chromatography, the separation is accomplished by the difference in the degree of exclusion or permeation of the elute molecules in the three dimensional network structure depending on the size of the solute molecule.

The presence of any of the substances represented by formulae (1) to (6) and/or their derivatives in the substance collected from the armpit can be qualitatively assayed by the retention time read from the chromatogram of the synthetic product and the human sample and the spectral peak information of the chromatogram obtained from the detectors.

For example, when a single mass spectrometer (MS) or two or more mutually connected mass spectrometers are used as the detector of a chromatographic process, mass spectral information (also referred to as "fragmentation pattern" or the "cleavage pattern") based on molecular weight and molecular structure for each of the components separated on the column can be obtained. Since the mass spectral information is inherent to each substance, the presence of any of the substances represented by formulae (1) to (6) and/or their derivatives in the substance collected from the armpit can be qualitatively assayed by using such mass spectral information.

When the detector used in the chromatography is one member or two or more connected members selected from visible and UV absorptiometer (visible/UV), infrared spectrometer (IR), Raman spectrometer, and nuclear magnetic resonance spectrometer (NMR), visible and UV (Vis/UV) absorption spectrum, infrared (IR) spectrum, Raman spectrum, and nuclear magnetic resonance (NMR) spectrum inherent to the molecular structure of each component are obtained from the components separated on the column.

Since the spectral information is unique to each substance, the presence of any of the substances represented by formulae (1) to (6) and/or their derivatives in the substance collected from the armpit can be qualitatively assayed.

In the chromatographic separation and assay system, size (area) of the peak in the chromatogram is proportional to the concentration of the substance corresponding to the peak. Accordingly, when any of the substances represented by formulae (1) to (6) and/or their derivatives is present, the content of such substance can be quantitatively assayed by using the area of the corresponding peak in the chromatogram as a reference.

When the synthesized product of the substance represented by formula (1) is used for the standard, calibration curves in various concentration ranges can be prepared by using the thus prepared standard, and the amount of the substance represented by formula (1) in the collected sample can be calculated by using the thus depicted calibration curves.

In the chromatographic separation and assay system, not only the qualitative assay of the presence of any of the substances represented by formulae (1) to (6) and/or their derivatives in the substance collected from the armpit, but also the quantitative assay of the amount of such substance can be conducted by using the size (area) of the peak in the chromatogram for reference. The body odor can then be determined on the basis of the comprehensive result of the analysis.

When a qualitative assay for the presence of any of the substances represented by formulae (1) to (6) and/or their derivatives in the substance collected from the armpit or a quantitative assay for the amount of such substance is conducted by using the chromatographic separation and assay system, the substances represented by formulae (1) to (6) and/or their derivatives may be chemically modified in order to improve selectivity and detection sensitivity of the assay, and the body odor can be determined by detecting the chemically modified substance. The body odor can also be determined by detecting both the non-chemically modified substance and the chemically modified substance.

In the chromatographic process, the method used in chemically modifying the substances represented by formulae (1) to (6) and/or their derivatives at their functional group and subsequently detecting the chemically modified substances is not particularly limited, and in an exemplary method, the substance collected from the armpit and the reagent for chemical modification (hereinafter also referred to as the chemical modification reagent) may be reacted for chemical modification and the chemically modified substance may be detected after the chromatographic separation (This method is hereinafter also referred to as the "pre-column modification"). Alternatively, the substances represented by formulae (1) to (6) and/or their derivatives in the substance collected from the armpit can be separated by a chromatographic process, and then, a chemical modification reagent may be added for chemical modification to thereby enable detection of the chemically modified substance (This method is hereinafter also referred to as the "post-column modification"). Such pre-column modification and post-column modification may also be used in combination.

The method used in the chromatographic process to chemically modify the substances represented by formulae (1) to (6) and/or their derivatives in order to improve the detection sensitivity, is not particularly limited. However, exemplary modifications which may be used in the liquid chromatographic process include incorporation of a chromophore (a compound exhibiting absorption for light in visible and UV range and compound having the character of emitting fluorescence) which improves detection sensitivity in at least one of the functional groups (for example, amino group, carboxy group, hydroxy group, carbonyl group, thiol group, and amide group) in the molecular structure of the substances represented by formulae (1) to (6) and/or their derivatives, and use of chemiluminescence and electrochemical activity. Exemplary modifications which may be used in the liquid chromatographic process include derivatization of the substance to a compound vaporizable in the given temperature.

The method used in incorporating an atomic group in at least one of the functional groups (for example, an amino group, carboxy group, hydroxy group, carbonyl group thiol group, and amide group) in the molecular structure of the substances represented by formulae (1) to (6) and/or their derivatives for improving the detection sensitivity is not particularly limited. In an exemplary method, a chromophore for improving the detection sensitivity is incorporated by means of various chemical reactions.

More specifically, a typical example in which a chromophore which absorbs visible or UV light or a chromophore which emits fluorescence incorporated in the amino group, carboxy group, or hydroxy group of the substance represented by formula (1) is the substance represented by the following formula (8).

Formula (8)

| $X_1=$ | $X_2=$ | $X_3=$ | Q: Chromophore (Typical examples) |
|---|---|---|---|
| —NH—SO$_2$—Q (Sulfonamide) | $\overset{O}{\underset{\|}{-C}}$—O—CH$_2$—Q (Ester) | —O—CH$_2$—Q (Ether) | HO—⟨benzene⟩—NO$_2$ Nitrophenol |

-continued

Formula (8)

| $X_1=$ | $X_2=$ | $X_3=$ | Q: Chromophore (Typical examples) |
|---|---|---|---|
| <br>(Carboxamide) | <br>(Isourea) | <br>(Urethane) | <br>Dinitrophenol |
| <br>(Thiourea) | <br>(Urea) | <br>(Ester) | <br>Azobenzene |
| <br>(Amide) | | | <br>Coumarin |
|  | | | <br>2,1,3-benzoxadiazole |
|  | | | <br>Naphthalene |
|  | | | <br>Acridine |

In formula 8, $R^1$, $R^2$ and $R^3$ are as defined above. $X_1$ shows typical examples in which a chromophore has been introduced in the amino group of the substance represented by formula (1); $X_2$ shows typical examples in which a chromophore has been introduced in a carboxy group of the substance represented by formula (1) ; and $X_3$ shows typical examples in which a chromophore has been introduced in a hydroxy group of the substance represented by formula (1).

For example, the amino group of the substance represented by formula (1) may be converted into other forms such as sulfonamide, carboxamide, thiourea, or amine. Similarly, the carboxy group of the substance represented by formula (1) may be converted to other forms such as ester, isourea, urea, or other forms. The hydroxy group may be converted to ether, urethane, ester, or other forms.

In incorporating a chromophore exhibiting absorption for visible and UV light or a chromophore having the character of emitting fluorescence which improves detection sensitivity in at least one of the functional groups (for example, amino group, carboxy group, hydroxy group, carbonyl group, thiol group, and amide group) in the molecular structure of the substances represented by formulae (1) to (6) and/or their derivatives, the chromophore used may be, for example, nitrophenol, dinitrophenol, azobenzene, coumarin, 2,1,3-benzoxadiazole, naphthalene, acridine, fluorescein, an analogue thereof, or other chromophore although the chromophore used is not particularly limited, and the functional group may be converted to the substituents $X_1$ to $X_3$ shown in formula (8) or an analog thereof.

The method used in incorporating a chromophore which improves detection sensitivity in at least one of the functional groups in the molecular structure of the substances represented by formulae (1) to (6) and/or their derivatives using various chemical reactions is not particularly limited, and such incorporation may be accomplished either by using a commercially available chemical modifier (derivatizing agent) or by freshly synthesizing a chemical modifier which can be used for the substances represented by formulae (1) to (6) and/or their derivatives as desired for use in the chemical modification.

Next, typical commercially available chemical modifiers (also referred to as the derivatizing agents) which can be used in the present invention is described.

Exemplary reagents which may be used in incorporating a (visible light and/or UV absorbing) chromophore in the amino group of the substances represented by formulae (1) to (6) and/or their derivatives include (a) an acyl chloride, (b) an allyl sulfonyl chloride, (c) a nitrobenzene, and (d) an isocyanate or isothiocyanate.

Exemplary acyl chlorides (a) include p-methoxybenzoyl chloride, m-toluoyl chloride, p-nitrobenzoyl chloride, and benzoyl chloride, and exemplary allyl sulfonyl chlorides (b) include toluene sulfonyl chloride (TSCl), benzenesulfonyl chloride (BSCl), and dimethylamino azobenzenesulfonyl chloride (DABSCl).

Exemplary nitrobenzenes (c) include 1-fluoro-2,4-dinitrobenzene (FDNB), trinitrobenzenesulphonic acid (TNBS), and 4-fluoro-3-nitrobenzotrifluoride (FNBT), and exemplary isocyanates or isothiocyanates (d) include phenyl isocyanate (PIC), naphthyl isocyanate (NIC), phenyl isothiocyanate (PITC), naphthyl isothiocyanate (NITC), 4-N,N'-dimethylamino azobenzene-4'-isothiocyanate, and p-phenyl benzoyl isothiocyanate.

Other examples include p-nitro benzyl bromide (p-NBBr), dansyl chloride (Dns-Cl), o-phthaldialdehyde (OPA), ninhydrin, and 1,2,3-perinaphthindan trione (Peri).

Exemplary reagents which may be used in incorporating a (fluorescent) chromophore in the amino group of the substances represented by formulae (1) to (6) and/or their derivatives include (a) sulfonyl chloride, (b) carbonyl chloride, (c) halogeno nitro benzofuran, (d) isocyanate or isothiocyanate, (e) Schiff base generating reagent and its related reagents.

Exemplary sulfonyl chlorides (a) include 5-dimethylamino naphthalene-1-sulfonyl chloride (Dns-Cl), 5-di-n-butyl aminonaphthalene-1-sulfonyl chloride (BNS-Cl) 6-N-methyl anilino naphthalene-2-sulfonyl chloride (Mns-Cl), 2-p-chlorosulfophenyl-3-phenylindone (Dis-Cl), 1,2-naphthalene benzimidazole-6-sulfonyl chloride, and 8-methoxy quinoline-5-sulfonyl chloride.

Exemplary carbonyl chlorides (b) include 9-fluorenyl-chloro methyl formate (FMOC), 2-naphthyl chloroformic acid (NCF), 2-dansylchloroethyl formate, and (R,S)-2-(p-chlorophenyl)-α-methyl-5-benzoxazole acetyl chloride, and exemplary halogeno nitrobenzofurans (c) include 4-chloro-7-nitro-2,1,3-benzoxadiazole (4-chloro-7-nitro benzofurazan; NBD-Cl), and 4-fluoro-7-nitro benzofurazan (NBD-F).

Exemplary isocyanates or isothiocyanates (d) include 9-isothiocyanate acridine, fluorescein isothiocyanate, 4-dimethylamino-1-naphthylisothiocyanate, 4-(benzyloxycarbonyl aminomethyl)phenylisothiocyanate, and 4-(dimethylamino naphthalene-1-sulfonylamino)phenylisothiocyanate.

Exemplary Schiff base generating reagents and its related reagents (e) include pyridoxal and pyridoxal phosphoric acid, 2-fluorene carboxyaldehyde, 1-pyrene carboxyaldehyde, o-phthaldialdehyde/alkylthiol (OPA/R—SH) reagent, 2-acetyl benzaldehyde/ethanethiol (OAB), ω-formyl-o-hydroxyacetophenone, and benzo-γ-pyrone, benzoin (2-hydroxy-2-phenylacetophenone).

Also included are 4-phenylspiro[furan-2(3H),1'-phthalan]-3,3'-dione (fluorescamine), 2-methoxy-2,4-diphenyl-3(2H)-furanone (MDPF), N-succinimidyl-2-naphthoxyacetate, and N-succinimidyl-1-naphthyl carbamate, 5-(4,6-dichloro-1,3,5-triazine-2-yl)aminofluorescein (DTAF).

Exemplary reagents which may be used in incorporating a (visible light and/or UV absorbing) chromophore in the carboxy group of the substances represented by formulae (1) to (6) and/or their derivatives include (a) phenacyl bromide, naphthacyl bromide, and their related compound, and (b) N-methylphthalimide derivative.

Exemplary phenacyl bromides, naphthacyl bromides, and their related compounds (a) include p-bromophenacyl bromide, phenacyl bromide, naphthacyl bromide, p-nitrophenacyl bromide, and 1-(4-hydroxyphenyl)-2-bromoethanone (4-HBE), and exemplary N-methyl phthalimide derivatives (b) include N-chloromethyl phthalimide (CIMPI), N-chloromethyl-4-nitro phthalimide (CIMNPI), and N-chloromethylisatin (CIMIS).

Also included are O-p-nitrobenzyl-N,N'-diisopropyl isourea (p-NBDI), 2-nitrophenylhydrazine, o-phenylenediamine, pyridinium dichromate, 2-methyl quinoxanol derivative, and imidazole.

Exemplary reagents which may be used in incorporating a (fluorescent) chromophore in the carboxy group of the substances represented by formulae (1) to (6) and/or their derivatives include fluorescent coumarin derivatives.

Exemplary fluorescent coumarin derivatives include 4-bromomethyl-7-methoxycoumarin (Br-Mmc), 4-bromomethyl-6,7-dimethoxycoumarin (Br-Mdmc), 4-bromomethyl-7-acetoxycoumarin (Br-Mac), 4-diazomethyl-7-methoxycoumarin, N,N'-dicyclohexyl-O-(7-methoxycoumarin-4-yl)methylisourea, N,N'-diisopropyl-O-(7-methoxycoumarin-4-yl)methylisourea, 9-bromomethyl acridine, 3-bromomethyl-6,7-dimethoxy-1-methyl-2(1H)-quinoxaline, naphthacyl bromide(2-bromoacetonaphthone), p-(anthroyloxy)phenacyl bromide (panacyl bromide), 1-bromoacetylpyrene, 9-chloromethylanthracene, and 9-anthryl diazomethane (ADAM).

Alternatively, the carboxy group of the substances represented by formulae (1) to (6) and/or their derivatives may be activated with a reagent such as oxalyl chloride, N-ethyl-N'-(3-dimethyl aminopropyl)carbodiimide, N,N'-carbonyldiimidazole, or 2-bromo-1-methylpyridinium iodide, and reacted with an alcohol or an amine.

For example, the substances represented by formulae (1), (3), and (4) and/or their derivatives may be reacted with oxalyl chloride to produce an acid chloride, and the acid chloride may be reacted with 9-aminophenanthrene or 1-naphthylamine in the presence of triethylamine to derivatize an amide compound which emits strong fluorescence.

Exemplary alcohols suitable for use in labeling an activated carboxylic acid with fluorescence include 9-hydroxymethyl anthracene, 2-dancylaminoethanol, and 4-hydroxymethyl-7-methoxy coumarin (HO-Mmc), and a fluorescent ester compound may be derivatized by using such an alcohol.

Exemplary reagents which may be used in incorporating a (visible light and/or UV absorbing) chromophore or an atomic group containing such chromophore in the hydroxy group of the substances represented by formulae (1) to (6) and/or their derivatives include anacyl chloride, phenyl isocyanate (PIC), and phenyldimethylsilyl chloride.

Exemplary acyl chlorides include benzoyl chloride, p-methoxybenzoyl chloride, p-nitrobenzoyl chloride, 3,5-dinitrobenzoyl chloride, and anthracene-9-carbonyl chloride.

Exemplary reagents which may be used in incorporating a (fluorescent) chromophore in the hydroxy group of the substances represented by formulae (1) to (6) and/or their derivatives include 7-methoxycoumarin-3-carbonyl azide (3-MCCA), 7-methoxycoumarin-4-carbonyl azide (4-MCCA), 7-(chlorocarbonyl methoxy)-4-methylcoumarin, 4-dimethylamino-1-naphthoyl nitrile, 1-anthroyl nitrile, 9-anthroyl nitrile, 2-methyl-1,1'-binaphthalene-2'-carbonyl nitrile, naphthalene boric acid, and phenanthrene boric acid.

Exemplary reagents which may be used in incorporating a (visible light and/or UV absorbing, or fluorescent) chromophore in the thiol group of the substances represented by formulae (1) to (6) and/or their derivatives include N-(9-acridinyl) maleimide (NAM), 4-Chloro-7-sulfobenzofurazan, ammonium salt (SBD-Cl), 4-fluoro-7-sulfobenzofurazan, ammonium salt (SBD-F), 4-fluoro-7-sulfamoyl benzofurazan (ABD-F), N-[4-(5,6-methylene dioxy-2-benzofuranyl)phenyl]maleimide (MBPM), N-[4-(6-dimethylamino-2-benzofuranyl)phenyl]maleimide (DBPM), N-[p-(2-benzimidazolyl)phenyl]maleimide, monobromobimane, 5,5-dithiobis(2-nitro benzoic acid), phenazine methosulfate, and o-phthalaldehyde/2-aminoethanol.

Exemplary chemical modification methods which may be used in incorporating a (visible light and/or UV absorbing) chromophore in the amido group of the substances represented by formulae (1) to (6) and/or their derivatives include color development by hydroxamic acid-iron chelate and color development of N-arylamide by azo dye generation.

Liquid chromatography is a process wherein the solute is separated by difference in the affinity for the stationary phase and the mobile phase, and the present invention can make use of various separation mechanisms (interaction between the elutes and the stationary phase). Examples include adsorption chromatography, partition chromatography, ion exchange chromatography, and size exclusion chromatography (gel filtration chromatography or gel permeation chromatography).

When the substances represented by formulae (1) to (6) is detected by gas chromatography and/or gas chromatography-mass spectrometer, at least one of the functional groups in the molecular structure of the substances represented by formulae (1) to (6) and/or their derivatives may be chemically modified based on various chemical reactions mainly for the purposes of imparting volatility, improving detection sensitivity, and improving resolution. The reagents suitable for such purposes are not particularly limited, and any suitable reagent may be used to enable the detection of the chemically modified substances represented by formulae (1) to (6) and/or their derivatives.

In an exemplary process, the substance represented by formula (1) may be imparted with volatility by esterifying the carboxy group of the substance represented by formula (1), and acylating the amino group of the substance represented by formula (1) for conversion into an N-acylalkyl ester which is a volatile derivative.

More specifically, examples of the alkyl ester in the above-mentioned N-acylalkyl ester include a methyl group, ethyl group propyl group, n- and isobutyl group, and n- and isoamyl group. Exemplary methods for the methyl ester synthesis include a method using diazomethane or boron trifluoride with methanol, and a method using trimethylsilyl diazomethane. Examples of the N-acyl group in the above-mentioned N-acylalkyl ester include an acetyl group, trifluoroacetyl group, pentafluoro propionyl group, and heptafluoro butyryl group. Examples of a method for introducing N-acyl group include a method in which anhydrous trifluoroacetic acid, trifluroacetic acid imidazole or the like is used.

Alternatively, the substance represented by formula (1) may be imparted with volatility by trimethylsilylating the carboxy group and/or the amino group in the substance represented by formula (1) to produce the N-trimethylsilylated form of the substance which is a volatile derivative.

Exemplary reagents which may be used for the trimethylsilylation include N-trimethylsilylimidazole (TMSI), N,O-bis(trimethylsilyl)trifluoroacetamide (BSTFA), N,O-bis(trimethylsilyl)acetamide (BSA), N-methyl-N-trimethylsilyl-trifluoroacetamide (MSTFA), N-trimethylsilyl dimethylamine (TMSDMA), N-methyl-N-trimethylsilyl-acetamide (MTMSA), and hexamethyldisilazane (HMDS).

The substance represented by formula (1) may also be imparted with volatility by esterifying the carboxy group of the substance represented by formula (1) by using methanol, ethanol, or butanol with hydrochloric acid, and trimethylsilylating the amino group of the substance represented by formula (1) for conversion into an N-trimethylsilylamino acid ester which is a volatile derivative.

In the present invention, determination of the body odor may also be conducted by detecting a substance known to be responsible for the body odor, for example, androstenones such as androstenone (5[]-16-androstene-3-one), androstenol (5[]-16-androstene-3[]-ol or 5[]-16-androstene-3β-ol), androstadienone (4,16-androstadiene-3-one), and/or its derivative; a lower aliphatic carboxylic acid such as acetic acid, propionic acid, butyric acid, isobutyric acid, valeric acid, isovaleric acid, 4-ethyl heptanoic acid, or 7-octenoid acid; aldehydes and ketones such as 1-octene-3-one or cis-1, 5-octadiene-3-one, in addition to the substances represented by formulae (1) to (6).

Immunochemical assay (also referred to as the "immunoassay") is an assay in which the amount of an antigen is chemically measured by means of an immunological reaction which is a means used in the body system for recognizing a molecule, namely, by the function ("antigen-antibody reaction") of capturing a particular substance called "antigen" by an "antibody" at a high sensitivity and a high selectivity to thereby inhibit the action of the antigen. In the present invention, such immunochemical assay may also be applied for detecting the substances represented by formulae (1) to (6) and/or their derivatives at a high sensitivity and a high selectivity.

In preparing an antibody against the substances represented by formulae (1) to (6), a spacer molecule or the like may be introduced as desired in the substances represented by formulae (1) to (6) to thereby increase their molecular weight before preparing the antibody.

The method used in detecting the amount of the substances represented by formulae (1) to (6) and/or their derivative in the sample collected from the armpit is not particularly limited. However, the substance detected may be labeled to realize a detection at a higher sensitivity. Such labeling may be accomplished, for example, using a radioisotope (radioimmunoassay), an enzyme (enzyme immunoassay), or a fluorescent dye or a chemiluminescent reagent.

In the present invention, the substances represented by formulae (1) to (6) can be detected by a wide variety of methods as described above, and when a reagent having an atomic group which exhibits absorption in the visible range (hereinafter also referred to as a "color reagent") is used as a chromophore, the color developed may be detected either with a visible-UV spectrophotometer or with the naked eye.

When the substances represented by formulae (1) to (6) are detected with the naked eye, the degree of the apocrine odor may be determined by preparing a color development standard sample indicating the relation between the color developed and the concentration of the labeled compound, and comparing the sample collected from the armpit with the thus prepared color development standard. For example, the substance of interest may be reacted with the color reagent or the like and the resulting aqueous solution may be filled in colorimetric tubes or impregnated in filter papers to thereby prepare color development standard samples, and the body odor may be determined by evaluating the color change of the substance collected from the armpit upon reaction with the color reagent by comparing with the color development standard sample. The determination of the body odor is thereby enabled. Alternatively, it is also possible to conduct the determination by direct evaluation of the color of the aqueous solution or by direct evaluation of the color of the test paper having the aqueous solution impregnated therein with the naked eye.

When the method as illustrated above is used, the amount of the substances represented by formulae (1) to (6) in the armpit can be qualitatively and/or quantitatively assayed, and an objective and quantitative determination of the possibility (potential) of the armpit smell, and in particular, the apocrine odor generation is enabled on the bases of the assay results.

Under the conditions when a large amount of the substances represented by formulae (1) to (6) are generated with the apocrine odor not yet generated, the apocrine odor can be deemed "latent". In such "latent" situation, an objective and quantitative determination of the body odor is not possible even if an assay using the component responsible for the apocrine odor directly for the index were conducted.

In contrast, the substance detected in the present invention is the precursor before turning into the main substance responsible for the apocrine odor, and therefore an objective and quantitative determination of whether the test subject is inclined to generate apocrine odor or not, namely, the possibility (potential) of the apocrine odor generation is thereby enabled.

The present invention has enabled a highly objective determination by using the substances represented by formulae (1) to (6) for the index, and also, a quantitative determination is realized by interpreting the assay data as the amount of the substance. The present invention is also capable of determining the effectiveness of the deodorant which is expected to have preventive action for the apocrine odor generation by detecting the substances represented by formulae (1) to (6).

For example, the substance represented by formula (2) which is the substance mainly responsible for the apocrine odor is a substance produced by the change of the substance represented by formula (1) by the action of, for example, a microorganism on the skin and therefore, an objective and quantitative determination of the effectiveness of the deodorant sample which is expected to have a preventive action for the apocrine odor can be accomplished by measuring the substance represented by formula (1) and/or the substance represented by formula (2).

More specifically, change in the amount of the substance represented by formula (1) and/or the substance represented by formula (2) can be compared by detecting the substance represented by formula (1) and/or the substance represented by formula (2) before and after applying the analyte which is expected to have the preventive action for the apocrine odor generation. This enables an objective and quantitative determination of the effect of the analyte in preventing the change of the substance represented by formula (1) to the substance represented by formula (2), namely, the effect of the analyte in preventing the apocrine odor generation.

In addition, since the substances represented by formulae (5) and (6) which are the main substances responsible for the apocrine odor are the substances respectively produced by the change of the substances represented by formulae (3) and (4) by the action of, for example, microorganisms on the skin, further detection of the substances represented by formulae (3) and (4) and/or the substances represented by formulae (5) and (6) enables determination of the effectiveness of the deodorant sample which is expected to have a preventive action on the apocrine odor generation at an improved objectivity and quantitative accuracy.

More specifically, change in the amount of the substances represented by formulae (3) and (4) and/or the substances represented by formulae (5) and (6) can be compared by detecting the substances represented by formulae (3) and (4) and/or the substances represented by formulae (5) and (6) before and after applying the analyte which is expected to have the preventive action for the apocrine odor generation. This enables an objective and quantitative determination of the effect of the analyte in preventing the change of the substances represented by formulae (3) and (4) to the substances represented by formulae (5) and (6) namely, the effect of the analyte in preventing the apocrine odor generation at an improved objectivity and quantitative accuracy.

In actually determining the effectivity of the deodorant sample which is expected to prevent the apocrine odor generation, the determination may be conducted by actually applying the analyte to the human armpit, collecting samples from the armpit before and after the analyte application, and detecting the substances represented by formulae (1) to (6) in the collected samples to thereby determine the effectiveness of the analyte.

In determining effectiveness of the deodorant sample which is expected to prevent generation of the apocrine odor, the substances represented by formulae (1) to (6) may be used either alone or in combination of two or more. In addition, the deodorant sample may also contain additives normally incorporated in an antiperspirant deodorant, for example, a solvent, stabilizer, antiperspirant, bactericide, antibacterial agent, surfactant, antioxidant, flavor, plant and extract.

EXAMPLES

Synthesis of 1,2-amino-7-hydroxy-5-methyl-5-propyl-4-thiaheptanoic acid (formula (9))

Formula 9

206 mg (1.39 mmol) of (S)-3-mercapto-3-methyl-hexane-1-ol and an equimolar amount of N-α-t-butoxycarbonyl-3-chloro-L-alanine (manufactured by Watanabe Chemical Industries, Ltd.) were dissolved in 4 mL of N,N-dimethylformamide, and to this solution, 2.6 equivalents of NaH (sodium hydride) was added in several aliquots while paying attention to heat generation and foaming. After completing the reaction, diethylether and ice water were added for phase separation. Ethyl acetate was added to the aqueous layer, and dilute hydrochloric acid was added for precipitation. After separation, the aqueous layer was again extracted with ethyl acetate. The ethyl acetate layers were combined, washed with water and saturated aqueous solution of sodium chloride, and dried for concentration to thereby obtain an oil.

Next, the target compound was purified by separation by HPLC on ODS column using MeCN/water/0.1% trifluoroacetic acid for the eluting solution. The eluted fractions of the target compound were combined, and after neutralization, MeCN was removed by distillation. After adding dilute hydrochloric acid and extracting with ethyl acetate, the solution was washed with water, and then, with saturated aqueous solution of sodium chloride. To the oil obtained by drying and concentration, 400 µL of 4N HCl/dioxane was added. The concentrate was again purified by separation by HPLC on ODS column using MeCN/water/0.1% trifluoroacetic acid for the eluting solution. The eluted fractions of the target compound were freeze dried to obtain 38 mg of viscous oil.

The synthesized product was evaluated for NMR spectrum by recording with Mercury 400Vx (manufactured by Varian). Chemical shift δ is shown below in ppm in relation to TMS which was used for the reference substance. The MS spectrum data recorded by LC-MS 2690 (manufactured by Waters) is also shown below. The NMR and MS spectrum obtained supported the structure of the target compound.

$^1$H-NMR (DMSO): 0.894 (t, $CH_3$), 1.250 (s, $CH_3$), 1.358 (m, $CH_2$), 1.447 (m, $CH_2$), 1.671 (t, $CH_2$), 2.881 (m, (S—)$CH_2$), 3.519 (t, $CH_2$—OH), 4.067 (t, CH—$NH_2$)

MS: m/z=226 (Ml$^{+1}$, relative strength 100%), m/z=122 (relative strength 33%)

2. Analysis of Apocrine Odor and its Precursor in Human Armpit (1) Analysis of Apocrine Odor 65 healthy Japanese males were randomly selected for the test subjects, and they continuously wore new white cotton T-shirt for 24 hours. The T-shirt was collected, and the part that had been in contact with the armpit was used for sensory evaluation by a panel of specialists (3 males and 2 females) for assessment of the type and the strength of the armpit smell.

<Items Evaluated in Determining the Armpit Smell Type>

Apocrine odor: a stinky smell with the smell like soy sauce or grapefruit

Acid odor (lower fatty acid odor) sour putrid smell

<Criteria for Strength of the Armpit Smell>
0: No smell
1: Slight smell
2: Weak smell
3: Moderate smell
4: Considerable smell
5: Strong smell As a result, 28 people had little armpit smell (with the score of the armpit smell strength of 1 or less) (group A), 21 people had weak armpit smell (with the score of the armpit smell strength of 2 or 3) (group B) and 16 people had strong armpit smell (with the score of the armpit smell strength of 4 or 5) (group C).

(2) Analysis of Apocrine Odor Precursor

The test subjects of this analysis were 3 subjects of group C who had strong apocrine odor and 3 subjects of group C who had no apocrine odor. About 2 mL of sweat was collected in a test tube from the armpit on both sides of each test subject in a room adjusted to a temperature of 40° C. and a humidity of 80%. The sweat (of each of the 6 samples) was filtered through cotton, and then, through a sterilization filter (0.2 μm), and 0.05N HCl aqueous solution was added to adjust the pH to 3.3. Next, the sweat was washed with distilled ether (0.4 mL×5 times), and then, with hexane (0.4 mL×5 times) to remove the oil soluble content. The residual solvent was removed by distillation using a rotary evaporator at room temperature for several hours. After filtration through the sterilization filter (0.22 μm), the solution was subjected to ultrafiltration. When the fraction having a molecular weight of up to 5000 was freeze dried, a transparent to slightly whitish viscous solid with no odor was obtained. All samples were stored at −40° C. until immediately before the analysis.

The samples prepared as described above were analyzed by HPLC-MS/MS mass spectroscopy.

<Measurement Conditions>

HPLC system: Agilent Model 1100 (manufactured by Agilent Technologies)

Analysis column: Inertsil ODS-3 (2.1 mm ID×250 mm)

Mobile phase: 50% (1% aqueous solution of acetic acid)/50% (1% methanol solution of acetic acid)

Mass spectrometer (MS/MS): API 4000 (Applied Biosystems/MDS Sciex)

Figure 1:
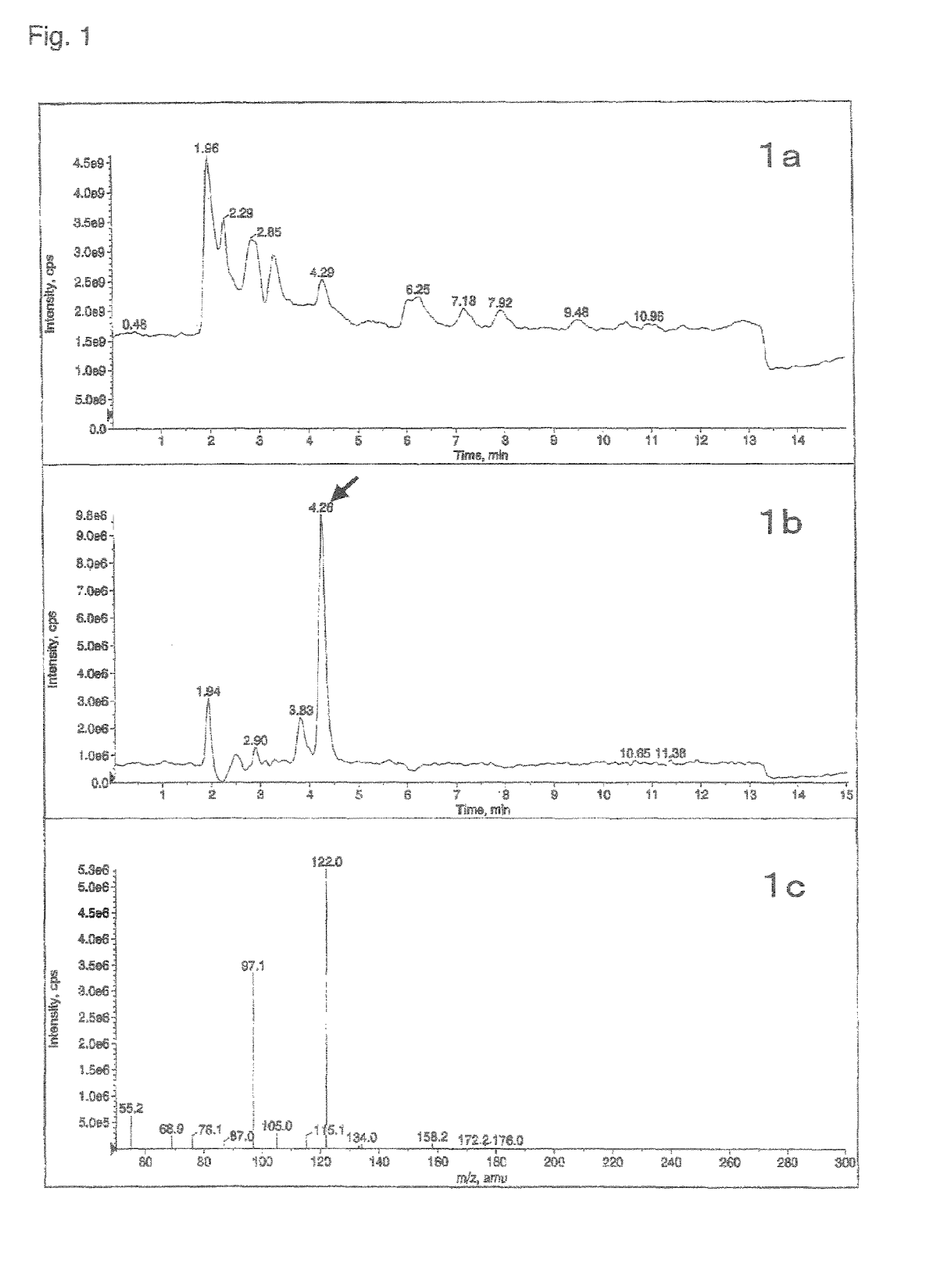
FIG. 1a shows the result of a normal ion scan (Q3 scan) for the sweat collected from a person with apocrine odor.
FIG. 1b shows the result of the product ion scan (m/z=236) for the sweat collected from a person with apocrine odor.
FIG. 1c shows the MS/MS spectrum for the peak at a retention time of 4.25 minutes.
Figure 2:
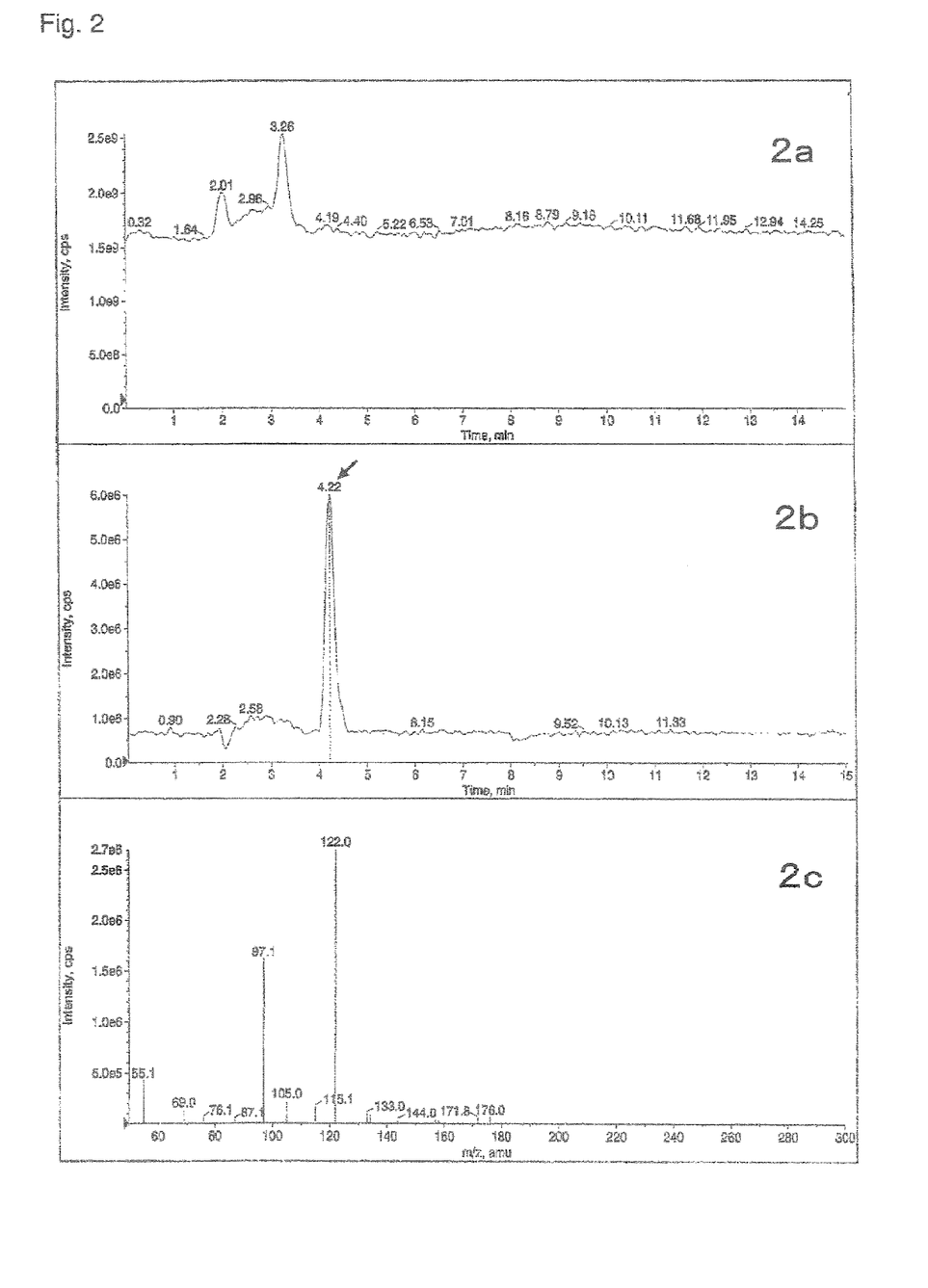
FIG. 2a shows the result of a normal ion scan (Q3 scan) for the 2-amino-7-hydroxy-5-methyl-5-propyl-4-thiaheptanoic acid (synthetic product).
FIG. 2b shows the result of the product ion scan (m/z=236) for the 2-amino-7-hydroxy-5-methyl-5-propyl-4-thiaheptanoic acid (synthetic product).
FIG. 2c shows the MS/MS spectrum for the peak at a retention time of 4.25 minutes.

The results of the analysis reveal that 2-amino-7-hydroxy-5-methyl-5-propyl-4-thiaheptanoic acid (formula (9)) was present in the sweat of the test subject having apocrine odor as shown in FIG. 1 (FIGS. 1a to 1c) and FIG. 2 (FIGS. 2a to 2c).

Figure 3:
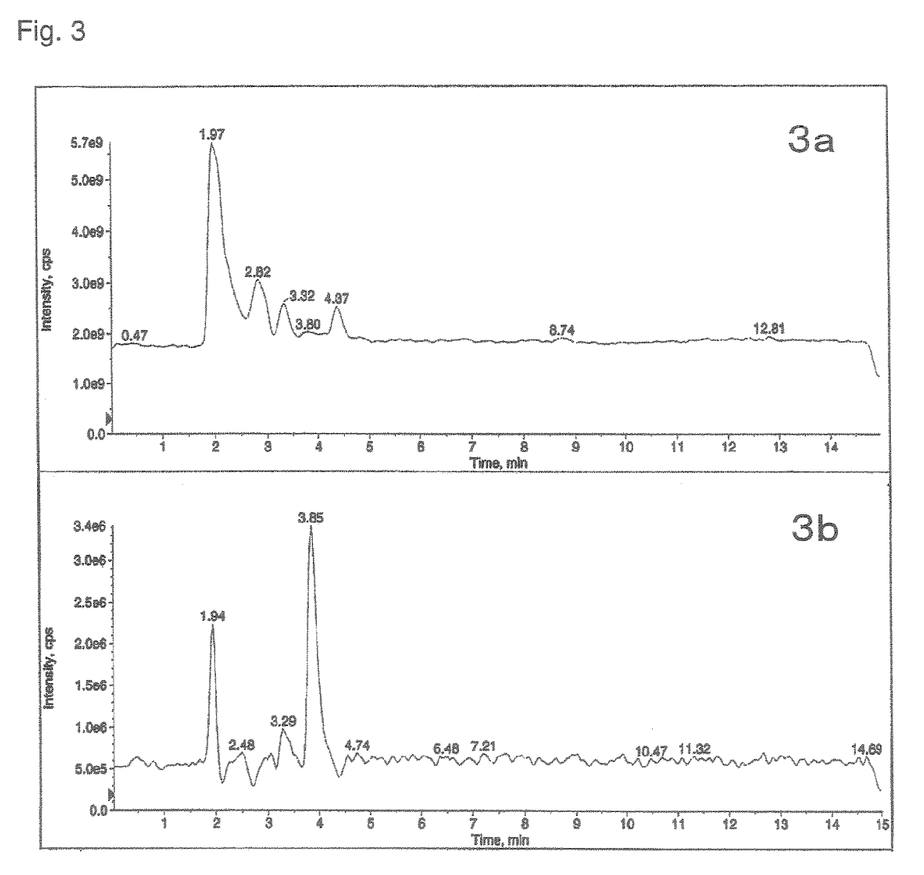
FIG. 3a shows the result of a normal ion scan (Q3 scan) for the sweat collected from a person without apocrine odor.
FIG. 3b shows the result of the product ion scan (m/z=236) for the sweat collected from a person without apocrine odor.

The results of the analysis reveal that 2-amino-7-hydroxy-5-methyl-5-propyl-4-thiaheptanoic acid (formula (9)) was absent in the sweat of the test subject having no apocrine odor as shown in FIG. 3 (FIGS. 3a and 3b).

(3) Analysis of the Mechanism of Apocrine Odor Generation

The test subjects of this analysis were 3 subjects of group C with considerable apocrine odor (with the score of the armpit smell strength of 4). 0.1 mg of 2-amino-7-hydroxy-5-methyl-5-propyl-4-thiaheptanoic acid (synthetic product, formula (9)) was dissolved in 0.1 mL of distilled water, and one armpit of the test subject was sprayed with this aqueous solution. The other armpit was sprayed with 0.1 mL of distilled water. After 8 hours, 5 expert panelists (3 males and 2 females) evaluated the armpit odor by sensory test. All of the expert panelists then answered that the stinky beastly smell like that of sulfur from 3-mercapto-3-methyl-hexane-1-ol was significantly stronger in the armpit of the side sprayed with the aqueous solution containing 2-amino-7-hydroxy-5-methyl-5-propyl-4-thiaheptanoic acid (synthetic product, formula (9)) compared to the armpit of the side sprayed only with the distilled water. In other words, it was demonstrated that 2-amino-7-hydroxy-5-methyl-5-propyl-4-thiaheptanoic acid decomposes into the 3-mercapto-3-methylhexane-1-ol on the skin of the human armpit.

3. Evaluation of Effectiveness of the Deodorant for Apocrine Odor

The test subject was one healthy American female in her thirties. The test subject was prohibited from using an antiperspirant deodorant or the like in the armpit from 10 days before the test. On the morning of the test, after confirming that the armpit odor was at the same level on both sides 0.3 g of the deodorant (stick type) was applied to one armpit. After 10 hours, sweat from both armpits was collected by wiping with a cotton gauze (5 cm×8 cm). The cotton gauze was divided in 8 equal pieces, fully wetted with 6 mL of distilled water, and the liquid absorbed in the gauze was squeezed for collection with a syringe. The gauze was wetted again with 6 mL of distilled water, and collected by squeezing with a syringe. After centrifugation, the extracts were combined, and washed twice with hexane (10 mL. The solvent was removed by distillation, and the residue was freeze dried, dissolved with mobile phase used for the HPLC, and subjected to ultrafiltration to collect the test sample having a molecular weight of up to 5,000. Standard solutions of different concentrations were separately prepared using 2-amino-7-hydroxy-5-methyl-5-propyl-4-thiaheptanoic acid. First, the standard solutions were analyzed by LC-MS/MS to depict a calibration curve of the 2-amino-7-hydroxy-5-methyl-5-propyl-4-thiaheptanoic acid (synthetic product). Next, the test samples were analyzed by LC-MS/MS to measure the amount of 2-amino-7-hydroxy-5-methyl-5-propyl-4-thiaheptanoic acid, namely, the precursor of the present invention, in the test samples. Rate of deodorization was thereby calculated.

<Measurement Conditions>

HPLC system: LC-10ADvp (manufactured by Shimadzu Corporation)

Analysis column: Inertsil ODS-3 (2.1 mm ID×250 mm)

Mobile phase: 50% (1% aqueous solution of acetic acid)/50% (1% methanol solution of acetic acid)

Mass spectrograph (MS/MS): API 2000 (Applied Biosystems/MDS Sciex) Q1/Q3 masses=236.10/122.00 amu <Deodorant Formulation>

| (Ingredient) | (% by weight) |
| --- | --- |
| Stearyl alcohol | 16 |
| Behenyl alcohol | 0.5 |
| Hardened castor oil | 3.5 |
| Decamethyl cyclopentasiloxane | 43 |
| Aluminum zirconium tetrachlorohydrex glycine complex | 24 |
| Talc | 7 |
| Fragrance | 1 |
| Others | 5 |
| Total | 100 |

As a result of the analysis, effectiveness of the deodorant (stick type) which was expected to suppress the generation of the apocrine odor was confirmed as shown in Table 1.

TABLE 1

| | | 2-amino-7-hydroxy-5-methyl-5-propyl-4-thiaheptanoic acid (the value measured, ng) | Deodoration rate (%) *1 |
|---|---|---|---|
| Right armpit | Application of 0.3 g of the deodorant | 44.4 | 73.4 |
| Left armpit | Not treated | 167.1 | |

*1: Deodoration rate (%) = [1 − {(the value measured for the side applied with the deodorant)/(the value measured for the non-treatment side)}] × 100

The invention claimed is:

1. A method for determining the effectiveness of a deodorant comprising:
quantitatively measuring a substance represented by the following formula (1):

Formula 1 wherein $R^1$ is a hydrogen atom or a methyl group, $R^2$ is an alkyl group containing 1 to 5 carbon atoms, and $R^3$ is a hydrogen atom or a methyl group.

2. The method of claim 1, wherein, in formula (1), $R^1$ is a methyl group, $R^2$ is a n-propyl group, and $R^3$ is a hydrogen atom.

3. A method for determining the effectiveness of a deodorant comprising:
quantitatively measuring a substance comprising formula (1) or a derivative thereof:

Formula 1 wherein
$R^1$ is a hydrogen atom or a methyl group,
$R^2$ is an alkyl group containing 1 to 5 carbon atoms, and
$R^3$ is a hydrogen atom or a methyl group.

4. The method of claim 3, wherein $R^1$ is a hydrogen atom.
5. The method of claim 3, wherein $R^1$ is a methyl group.
6. The method of claim 3, wherein $R^2$ is an alkyl group having 2 or 3 carbon atoms.
7. The method of claim 3, wherein $R^2$ is a methyl group.
8. The method of claim 6, wherein $R^2$ is an alkyl group having 4 or 5 carbon atoms.
9. The method of claim 3, wherein $R^3$ is a hydrogen atom.
10. The method of claim 3, wherein $R^3$ is a methyl group.
11. The method of claim 3, wherein in formula (1), $R^1$ is a methyl group, $R^2$ is a n-propyl group, and $R^3$ is a hydrogen atom.
12. The method of claim 3, comprising quantitatively measuring a derivative of formula (1) in which the amino and/or carboxy group of formula (1) has formed a peptide bond.
13. The method of claim 3, wherein the compound of formula (1) is selected from the group consisting of:

2-amino-7-hydroxy-5-propyl-4-thiaheptanoic acid (1b)

2-amino-7-hydroxy-5-ethyl-4-thiaheptanoic acid (1c)

2-amino-7-hydroxy-5-methyl-6-methyl-4-thiaheptanoic acid (1d)

and 2-amino-7-hydroxy-5-ethyl-6-methyl-4-thiaheptanoic (1e)

or derivative thereof.

14. The method of claim 3 which quantifies said substance using a chromatographic method.
15. The method of claim 3 which quantifies said substance using an immunological method.

* * * * *

UNITED STATES PATENT AND TRADEMARK OFFICE
CERTIFICATE OF CORRECTION

PATENT NO.         : 7,608,459 B2
APPLICATION NO.    : 11/568778
DATED              : October 27, 2009
INVENTOR(S)        : Masayuki Yabuki et al.

It is certified that error appears in the above-identified patent and that said Letters Patent is hereby corrected as shown below:

Column 30, line 25, delete formula (1c) in its entirety and replace with the following:

--(1c) 2-amino-7-hydroxy-5-ethyl-4-thiaheptanoic acid

--

Signed and Sealed this

Nineteenth Day of January, 2010

David J. Kappos
*Director of the United States Patent and Trademark Office*